United States Patent
Lacza et al.

(10) Patent No.: US 9,770,530 B2
(45) Date of Patent: Sep. 26, 2017

(54) TISSUE SUBSTITUTE MATERIAL WITH BIOLOGICALLY ACTIVE COATING

(71) Applicant: LACERTA TECHNOLOGIES INC., Winston-Salem, NC (US)

(72) Inventors: Zsombor Lacza, Csopak (HU); István Hornyák, Miskolc (HU); Pálma Kalugyer, Érd (HU); Edit Madácsi, Dunatetétlen (HU)

(73) Assignee: Lacerta Technologies Inc., Raleigh, NC (US)

( * ) Notice: Subject to any disclaimer, the term of this patent is extended or adjusted under 35 U.S.C. 154(b) by 0 days.

(21) Appl. No.: 14/767,008

(22) PCT Filed: Feb. 11, 2014

(86) PCT No.: PCT/IB2014/058915
§ 371 (c)(1),
(2) Date: Aug. 11, 2015

(87) PCT Pub. No.: WO2014/122631
PCT Pub. Date: Aug. 14, 2014

(65) Prior Publication Data
US 2015/0367032 A1   Dec. 24, 2015

Related U.S. Application Data

(60) Provisional application No. 61/763,002, filed on Feb. 11, 2013.

(30) Foreign Application Priority Data

Feb. 11, 2013   (EP) .................................... 13154848

(51) Int. Cl.
*C09D 105/04*   (2006.01)
*C09D 105/06*   (2006.01)
(Continued)

(52) U.S. Cl.
CPC ............... *A61L 27/34* (2013.01); *A61L 27/36* (2013.01); *A61L 27/365* (2013.01);
(Continued)

(58) Field of Classification Search
CPC ..... C08L 5/06; C08L 5/04; C08L 5/08; C09D 105/04; C09D 105/06; C09D 105/08;
(Continued)

(56) References Cited

U.S. PATENT DOCUMENTS

2002/0182265 A1* 12/2002 Burrell .................. A01N 59/16
424/618
2003/0004568 A1*  1/2003 Ken .................. A61B 17/12022
623/1.46
(Continued)

FOREIGN PATENT DOCUMENTS

WO   2012/094708 A1   7/2012

OTHER PUBLICATIONS

Swanson et al. (J Biomed mater Res Part A: 2011; 97A:167-176).*
(Continued)

*Primary Examiner* — Ernst V Arnold
(74) *Attorney, Agent, or Firm* — Jason D. Voight

(57) ABSTRACT

The present invention relates to a tissue substitute material for implantation, comprising (a) a substrate to be implanted covered with (b) a controlled release coating containing (c) at least one biologically substance that decreases bacterial growth, wherein the (b) controlled release coating is a bioavailable, biocompatible polymer material and wherein the (c) at least one biologically active substance that decreases bacterial growth. The present invention also relates to a method to prepare the tissue substitute material, as wells the uses thereof.

20 Claims, 2 Drawing Sheets

(51) Int. Cl.
- *A61L 27/34* (2006.01)
- *A61L 27/36* (2006.01)
- *A61L 27/54* (2006.01)
- *A61L 27/58* (2006.01)
- *C08L 5/04* (2006.01)
- *C08L 5/06* (2006.01)
- *C08L 5/08* (2006.01)
- *C09D 105/08* (2006.01)

(52) U.S. Cl.
CPC ....... *A61L 27/3608* (2013.01); *A61L 27/3645* (2013.01); *A61L 27/54* (2013.01); *A61L 27/58* (2013.01); *C08L 5/04* (2013.01); *C08L 5/06* (2013.01); *C08L 5/08* (2013.01); *C09D 105/04* (2013.01); *C09D 105/06* (2013.01); *C09D 105/08* (2013.01); *A61L 2300/406* (2013.01); *A61L 2300/414* (2013.01); *A61L 2300/606* (2013.01); *A61L 2420/02* (2013.01); *A61L 2430/02* (2013.01); *A61L 2430/06* (2013.01)

(58) Field of Classification Search
CPC ......... A61L 2300/406; A61L 2300/414; A61L 2300/606; A61L 2420/02; A61L 2430/02; A61L 2430/06; A61L 27/34; A61L 27/36; A61L 27/3645; A61L 27/365; A61L 27/54; A61L 27/58; G01R 33/481; G01R 33/4816; G01R 33/4828; G01R 33/5608; G01R 33/5615; G01R 33/5616

See application file for complete search history.

(56) References Cited

U.S. PATENT DOCUMENTS

| | | | | |
|---|---|---|---|---|
| 2004/0071776 | A1* | 4/2004 | Boudy | ............... A61L 27/16 424/486 |
| 2005/0196497 | A1* | 9/2005 | Soedjak | ............... A23L 2/02 426/324 |
| 2009/0324683 | A1* | 12/2009 | Evans | ............... A61K 9/0024 424/426 |
| 2010/0292326 | A1 | 11/2010 | Lacza et al. | |

OTHER PUBLICATIONS

Hervas et al. (International Journal of Pharmaceutics 1998;169:115-119).*
Jaya et al. (Journal of Microencapsulation 2009;26(2):143-153).*
Romero et al. (Indian J. Ophthalmol. 2009;57(5):341-344).*

* cited by examiner

TISSUE SUBSTITUTE MATERIAL WITH BIOLOGICALLY ACTIVE COATING

This application is the national stage of International Application PCT/IB2014/058915, filed Feb. 11, 2014, and claims priority to provisional application Ser. No. 61/763,002 filed Feb. 11, 2013.

The present invention relates to a tissue substitute material for implantation, comprising (a) a substrate to be implanted covered with (b) a controlled release coating containing (c) at least one biologically substance that decreases bacterial growth, wherein the (b) controlled release coating is a bioavailable, biocompatible polymer material and wherein the (c) at least one biologically active substance that decreases bacterial growth. The present invention also relates to a method to prepare the tissue substitute material, as well as the uses thereof.

BACKGROUND

Surgical treatment of musculoskeletal diseases relies more and more on the long-term implantation of foreign materials such as bone substitutes, endoprosthesis, degradable scaffolds and plastic components. Since the immune system is not adapted well to fight bacterial infection associated with these foreign materials, septic complications are a growing concern for the orthopedic community (Antoci et al. Clin Orthop Relat Res. 2007; 461:81-87 Antoci et al. J Orthop Res. 2007; 25:858-866). Due to the low metabolic rate of bone tissue and the formation of bacterial biofilm, it is difficult to reach the required local concentration of antibiotics whether it is applied systemically or on the spot during surgery (Costerton et al. Science. 1999; 284:1318-1322, Ketonis et al. Antimicrob Agents Chemother. 2011; 55:487-494., Stoodley et al. Annu Rev Microbiol. 2002; 56:187-209). In the general practice, local treatment is typically applied to support systemic antibiotics, the most frequently used drugs include amoxicillin, cephalexin, gentamicin, sulfamethoxazole, ciprofloxacin and vancomycin, applied in cement (Buchholz et al. Clin Orthop Relat Res. 1984:96-108, Trippel et al. J Bone Joint Surg Am. 1986; 68:1297-1302, Wininger et al. Antimicrob Agents Chemother. 1996; 40:2675-2679.), beads and impregnated bone (Barckman et al. J Biomed Mater Res B Appl Biomater. 2013, Buttaro et al. Hip Int. 2010; 20:535-541, Ketonis et al. Clin Orthop Relat Res. 2010; 468:2113-2121, Ketonis et al. Bone. 2011; 48:631-638, Melichercik et al. Folia Microbiol (Praha). 2012; 57:459-462, Winkler et al. Int J Med Sci. 2009; 6:247-252). In addition, off-label use of these antibiotics mixed by hand with the carrier bone substitute is often performed when the required antibiotic-carrier combination is not available off-the-shelf (Mathijssen et al. BMC Musculoskelet Disord. 2012; 13:44). Whether the applied dose and the release kinetics of such mixtures is optimal or at least adequate for the intended purpose is unknown, but it is still the best way a surgeon can deal with these challenging situations.

The therapeutic goal of local antibiotic use in combination with endoprostheses can be categorized into three distinct case types: 1, prevention of early infection at a primary prosthesis implantation procedure, 2, inhibiting infection at aseptic prosthesis revisions where the probability of an already ongoing low-grade infection is high and 3, treatment of massive infections at septic revisions (Gehrke et al. Hip Int. 2012; 22 Suppl 8:S40-45, Klatte et al. J Arthroplasty. 2013). These cases pose differing challenges for the antibiotics summarized in Table 1.

TABLE 1

Technical requirements against a local antibiotic formulation in the 3 main categories of orthopedic use in endoprosthesis surgery.

| | Medical purpose | Probability of infection | Antibiogram | Required length of local antibiotic treatment | Typical local antibiotic formulation |
|---|---|---|---|---|---|
| Primary implantation | Prevention of infection arising from contamination at surgery or early post-op | 0.5-2% | Not available | 1-2 days or until the surgical site is open through drainage | Antibiotic bone cement, off-the-shelf |
| Aseptic revision | Prevention of infection arising from either contamination or a low-grade infection | n/a | Not available, or its reliability is low | 1-2 days or until the surgical site is open through drainage. Longer if low-grade infection is suspected. | Antibiotic bone cement, bone substitutes, freehand use of local antibiotic powder or solution |
| Septic revision | Eradication of bacterial infection | 100% | Available | Several weeks | Antibiotic bone cement, freehand use of local antibiotic powder or solution. Bone substitutes are contraindicated. |

It is evident that even if one focuses only on antibiotic bone substitutes several formulations should be available in order to meet these diverging criteria (Zilberman et al. J Control Release. 2008; 130:202-215). One way of modifying the release kinetics of drugs in an implantable formulation is to couple the active agent with biodegradable polymers. Two well known materials, which are frequently used to form biodegradable coatings are chitosan (Chi) and sodium alginate (Na-Alg) (Akter et al. Radiation Physics and Chemistry. 2012; 81:995-998, Buranapanitkit et al. Clin Orthop Relat Res. 2005:236-241). These bio-polymers have been investigated over a wide scale including the preparation of fibers, nanoparticles and even bone substitutes, thus they pose a very low risk of toxicity (Dai et al. J Biomed Biotechnol. 2009; 2009:595126, Sanna et al. Int J Nanomedicine. 2012; 7:5501-5516, Zhou et al. Int J Nanomedicine. 2013; 8:877-887). Chitosan is prepared from shrimp-shell chitin with hydrolysis and is only soluble in acidic media. It forms excellent films and coatings and in case it is added to acidic forms of drugs it can slow down release and degradation as described in WO 2009/050527 A1. 2009. Alginate derivatives such as alginic acid or sodium alginate are produced from seaweed species. The main feature of sodium alginate is that it is insoluble in acidic solutions and forms a biodegradable film that can be turned into water insoluble calcium alginate (Ca-Alg), which can act as a barrier for drug coatings. The general view of the surgical community is that local use of antibiotics without any carrier is only effective for the first few days post-op, however, this view is not supported by reliable experimental data. Theoretically it can be hypothesized that fixation of the antibiotic with physico-chemical means such as freeze-drying or embedding in polymer coatings may prolong the release of drugs, however, it is unknown if these procedures can meet the requirements detailed in Table 1.

The market of bone fillings and bone substitutes consist of a wide range of materials and biologically active components respectively.

As bone substitute materials, we can mention examples like tricalcium phosphate, calcium sulfate, hydroxyapatite and human bone grafts. The main functions of the substitute materials are mechanical strength, healing and structural re-integration of cells and tissues.

Biologically active coatings or pharmaceutically active agents include components (e.g. growth factors, antibiotics), which can enhance bone formation, cell adhesion, cell differentiation or can prevent bacterial infection.

More specifically defined bone substitutes include polymers that e.g. comprises of polylactic acid, polyglycolic acid or poly(lactic-co-glycolic acid). WO2012094708 discloses a synthetic bone replacement material that can prevent potential infection compared to human derived bone allograft. Also during human allograft disinfection prior to implantation, there is also a risk that the bone contains traces of disinfectant. However, Liban Chang et al. (Formosan Journal of Musculoskeletal Disorders 2 (2011) 55-61) showed with the use of supercritical $CO_2$ a simple and safe method can be achieved to process human bone allograft disinfection.

Still till nowadays, bone is the most convenient grafting material, and according to the review article of Konstantinos Anagnostakos et al. (International Journal of Biomaterials, Volume 2012, Article ID 538061, 9 pages). This article describes a type of pharmaceutically active components, mainly focusing on antibiotics. The idea of mixing bone with antibiotics is known in the art, (De Grood et al. Ned Tijdschr Geneeskd, vol. 91.III.32, pp. 2192-2196, 1947) was the first to report on mixing penicillin with cancellous bone when filling bone defects in 1947. However emerging interest only appeared in the 1980s of mixing bone with biologically active components. The coating methods used were limited, manual mixing or incubation in solvents was the most frequently used techniques.

The used biologically active coatings mainly focus on antibiotics and cell adhesion and/or growth enhancers. As disclosed in the US Patent Application No. 20090324683 describing a biologically active coating (Bruce G Evans et al., "Controlled Release Tissue Graft Combination Biomaterials") transforming growth factors (TGFs), bone morphogenetic proteins (BMPs), fibroblast growth factors (FGFs), parathyroid hormone derivatives (PTHs), Nell-1, statins, certain known osteoinductive peptides (e.g., P15, truncated PTHs or collagens), insulin-like growth factors (IGFs), and/or platelet-derived growth factors (PDGFs), or their respective therapeutic nucleotide transgenes may be used for this purpose.

The present invention comprises of tissue substitute material that is intended to be used for human implantation purposes, mainly to enhance cell adhesion and cell growth and to prevent bacterial infection. The used grafting material may be any such material customary in the field. The controlled release coating according to the invention may be used on any surface that enables the adsorption of the monomers/polymers utilized, or on any surface that may be made artificially adsorbent. In a preferred aspect, the grafting material is human tissue, preferably from the musculoskeletal system, more preferably cancellous bone allograft, which we found to be optimal for vascularisation and re-integration of existing tissues. The used antibiotic agents were selected by comparing practical results among these practical reasons are water solubility, heat stability and mechanical properties. The controlled release coating materials, which were chosen, are biocompatible, bioavailable. All the used materials used are already used in pharmacological products.

Accordingly, the present invention provides a tissue substitute material for implantation, comprising (a) a substrate made of the tissue to be implanted covered with (b) a controlled release coating containing (c) at least one biologically active substance that decreases bacterial growth, wherein the (b) controlled release coating is a bioavailable, biocompatible polymer material selected from the group consisting of: chitosan, alginic acid or a combination thereof, or any one of those in combination with pectin; and wherein the (c) at least one biologically active substance that decreases bacterial growth can be any antibiotics or a mixture thereof.

For the present invention, US 20090324683 could be considered as the closest prior art, since it relates to the same technical field and provides solutions similar in their scope. In view of this, to avoid unnecessary inflation of the extent of the present specification, Section A thereof with the definitions is included herein by reference.

US 20090324683 discloses tissue graft combination biomaterials comprising one or more agents, including bioactive agents, pharmaceutically active agents, or combinations thereof, which can be combination biomaterials of one or more agents and one or more substrates suitable for use as tissue graft materials. The disclosed combination tissue graft biomaterial comprises a biocompatible substrate; a degradable natural or synthetic polymer coated over the substrate surface; and a bioactive agent or pharmaceutically active agent encapsulated by the polymer matrix. By "encapsulated" is meant that the agent(s) can be either incorporated into the polymer or into or onto the substrate and covered by the polymer coating, such that release of the agent(s) from the combination tissue graft biomaterial is hindered and controlled by the polymer coating barrier and its degradation at the site of application. Also disclosed are methods of making the disclosed tissue grafts to select the rate of controlled release of bioactive agents, pharmaceutically active agents, or combinations thereof to produce therapy at the implant site.

First and foremost it should be noted that US 20090324683 describes a general, conceptualized controlled release system. This disclosure is expanded with laundry list type sections on all of the support component, the polymer component and the active agent. Contrary to the countless of the possible combinations of these three main constituent of the system, US 20090324683 gives experimental results only for polycaprolactone (PCL) as the controlled release polymer coating material, and a couple of antibiotics. It is evident that the controlled release properties of such a tripartite system are more dependent on the polymer component than either of the support or the active agent. In this respect, US 20090324683 clearly lacks enabling disclosure for the polymers in general.

More significantly, the example provided is for PCL, which is a water-insoluble material, the monomer of which is applied in acetone mixed with the active ingredients. It is apparent that such method is very limited in its application, may work with the antibiotics suggested in the experimental part of US 20090324683, but clearly not a good solution for more sensitive biomolecules, such as growth factors, hormones, etc. In summary, PCL coating can either be constructed using an organic solvent or heating the polymer to at least 50° C., which circumstances decrease biocompatibility and increase decomposition of the incorporated biologically active substance.

Further, there is not a single mention in US 20090324683 for the use of combination of polymers. It is clear, as detailed below that the combination of different polymers with pectin provides significantly improved properties for the controlled release coating. No such advantages could be foreseen based on the prior art.

Accordingly, to highlight the novelty and inventiveness of the present invention over the prior art, it is once again emphasized that the invention provides a bone substitute material for implantation, comprising the bone allograft to be implanted covered with a controlled release coating made of a polymer wherein the monomers of said polymer are water-soluble, and containing at least one biologically active substance that decreases bacterial growth. The polymer materials used form a valid selection over the prior art.

In addition, the methods of preparation of such a bone substitute material according to the invention are also clearly novel and inventive over the prior art as the use of organic phase may be completely eliminated during the manufacturing process. Further, the inventive production process uses a two-stage polymerization, which is made possible by the physic-chemical properties of the polymers used. Both chitosan and alginate that forms the base of the controlled release coating only form the polymer from the monomers where certain chemical changes induce the polymerization. The polymers used in the present invention are constructed from water soluble starting materials, all of them are low molecular weight substances (3-25 kDa).

In another aspect, the present invention provides a method for preparing a tissue substitute material for implantation, comprising (a) preparing a homogenous coating on the substrate to be implanted from at least one biologically active substance that decreases bacterial growth;

(b) preparing a film coating from the water-soluble monomers of a biocompatible polymer material selected from the group consisting of chitosan and alginic acid, or a combination thereof, or any one of those in combination with pectin;

(c) drying the water-soluble film coating;

(d) converting the water soluble film coating into water insoluble film coating;

(e) drying the water-insoluble film coating.

In a preferred embodiment, the invention provides a tissue substitute material or method wherein the tissue is a tissue from the musculoskeletal system, preferably bone tissue, cartilage tissue or tendon tissue.

In another preferred embodiment, the invention provides a tissue substitute material or method wherein the tissue is bone allograft.

In a particularly preferred embodiment, the invention provides a tissue substitute material for implantation which is a bone substitute material for implantation, comprising (a) the bone allograft to be implanted covered with (b) a controlled release coating containing (c) at least one biologically active substance that decreases bacterial growth, wherein the (b) controlled release coating is a bioavailable, biocompatible polymer material selected from the group consisting of: chitosan, alginic acid or a combination thereof, or any one of those in combination with pectin; and wherein the (c) at least one biologically active substance that decreases bacterial growth can be any antibiotics or a mixture thereof.

In another particularly preferred embodiment, the invention provides a method for preparing a tissue substitute material for implantation, which is a bone allograft material for implantation, comprising (a) preparing a homogenous coating on the bone allograft material from at least one biologically active substance that decreases bacterial growth;

(b) preparing a film coating from the water-soluble monomers of a biocompatible polymer material selected from the group consisting of chitosan and alginic acid, or a combination thereof, or any one of those in combination with pectin;

(c) drying the water-soluble film coating;

(d) converting the water soluble film coating into water insoluble film coating;

(e) drying the water-insoluble film coating.

In another embodiment, the invention provides a tissue substitute material or method, wherein the substrate is a known tissue substitute, preferably bone substitute, more preferably selected from the group consisting of implants made from metal, plastic or other materials, and standalone polymer material suitable for the preparation of the coating, preferably alginate beads.

In this specific embodiment of the invention, a particularly preferred substrate is the standalone polymer material that otherwise also used for the preparation of the coating. More particularly, the combination of pectin and sodium alginate results in a unique polymer combination, which can be used not only as coating, but as solid microspheres.

The art discloses several substrate systems which are formed from this kind of polymer materials. However, pectin is not used as a gelling agent or thickener according to the present invention, but as a water soluble biodegradable part of a two or more component biocompatible polymer system, which is partly water insoluble. The inventors surprisingly found that the water soluble Na-alginate part of the complex polymer can be selectively converted into water insoluble Ca-alginate but leaves the water soluble pectin part intact with choosing the appropriate Ca2+ source and the time of Na—Ca conversion. The film coating or microsphere prepared this way enables pectin to elute freely in the aqueous media depending on the concentration and distribution in the polymer system, while Ca-alginate mainly releases the drug during decomposition. Thus the release of the incorporated drug content can increase or decrease depending on the pectin-alginate (as water soluble-water insoluble) ratio.

In another preferred embodiment, the invention provides a tissue substitute material wherein the (b) controlled release coating is alginic acid pectin copolymer.

In a further preferred embodiment, the invention provides a tissue substitute material or method wherein the (b) controlled release coating essentially consists of alginic acid within the range of 70 to 90% and pectin within the range of 10 to 30%.

In another preferred embodiment, the invention provides a tissue substitute material or method wherein the (c) at least one biologically active substance that decreases bacterial growth is selected from the group consisting of gentamicin, ciprofloxacin, vancomycin, amoxicillin.

In another preferred embodiment, the invention provides a tissue substitute material or method, further comprising other biologically active ingredients to enhance cell migration, adhesion and growth.

In particularly preferred embodiments, the invention provides a tissue substitute material or method according said biologically active ingredient to enhance cell migration, adhesion and growth is selected from the group consisting of growth factors including PDGF, TGF-/315 vascular endothelial growth factor, basic fibroblast growth factor (bFGF), and epidermal growth factor; albumin, platelet rich plasma (PRP), platelet pure plasma (PPP) and platelet rich fibrin (PRF) and other blood separation products that contain cell growth and/or cell migration enhancing agents.

In a preferred embodiment of the method of the invention, the antibiotic coating is prepared in step (a) by freeze drying, solvent evaporation or vacuum evaporation. In a preferred embodiment of the method of the invention, the film coating is prepared in step (a) spraying or casting.

In another preferred embodiment of the method of the invention, the drying in step (c) and/or (e) is accomplished in a drying chamber or exsiccator, or by using moderate heating and vacuum. In a further preferred embodiment of the method of the invention, in step (d), the conversion of the soluble film coating into water insoluble film coating is accomplished by using a $Ca^{2+}$ ion containing solution, preferably within the range of 1 to 20%.

In another aspect, the invention provides the tissue substitute material, preferably a bone allograft material for implantation according to the invention or the bone allograft material obtainable by the method according to the invention, for the treatment of a condition, disease or disorder selected from the group consisting of:

i, prevention of bone infection. e.g. Surgery, contaminated wounds, open fractures, implantation of any foreign material, presence of any foreign material, filling the cavity of bone cysts, treatment of aseptic non-union;

ii, prevention of re-infection. e.g. Revision surgery after septic complications, reconstructive surgery after traumatic or other bone loss, treatment of posttratumatic or post-septic non-union;

iii, treatment of bone infection. e.g. Acute or chronic osteomyelitis, ostitis, septic non-union, septic implants or prosthetic devices or any other foreign material, including projectiles.

In another aspect, the invention provides a method for treating a condition, disease or disorder selected from the group consisting of:

i, prevention of bone infection. e.g. Surgery, contaminated wounds, open fractures, implantation of any foreign material, presence of any foreign material, filling the cavity of bone cysts, treatment of aseptic non-union;

ii, prevention of re-infection. e.g. Revision surgery after septic complications, reconstructive surgery after traumatic or other bone loss, treatment of posttratumatic or post-septic non-union;

iii, treatment of bone infection. e.g. Acute or chronic osteomyelitis, ostitis, septic non-union, septic implants or prosthetic devices or any other foreign material, including projectiles, wherein said method comprising the step implanting the bone allograft material for implantation according to the invention or the bone allograft material obtainable by the method according to the invention.

DETAILED DESCRIPTION

The present invention demonstrates that using physico-chemical methods it is possible to produce an antibiotic coating with biopolymers that can modify the release kinetics of antibiotic impregnated bone grafts in order to reach either complete unloading in 48 hours or sustained release for up to 50 days.

A critical limitation in one-stage revision surgery is the extent of bone loss. Ideally, one would perform elaborate bone replacement techniques in order to build a suitable biological base for a new implant, however, bone grafts are viewed as contraindicated in these procedures due to the high probability of infection. Impregnation of bone grafts with an antibiotic solution by hand-mixing them in the OR is generally applied as a preventive measure, however, most surgeons would consider this technique inadequate for septic cases. This view in confirmed by data from the present study. Even when the antibiotics are incubated for a day and then freeze-dried onto the bone, the majority of the drug is released during the first day after placing the graft in water. This release kinetic may be suitable for fighting perioperative infection when the implant may be contaminated during surgery or from the patient's skin through the surgical wound or drainage tubes, but this timeframe is inadequate to eradicate massive infections.

Dosing of antibiotics in combination with a bone substitute is a challenge. In most cases the volume of the required bone graft is only determined during surgery so pre-determining the required dose is only realistic with large margins. Moreover, the amount of antibiotic, which is implanted into a patient is set by the amount of bone graft, as dosing of the drug follows the 'dosing' of the graft. The highly variable spatial conformations add a further degree of freedom to the equation. One would assume that tightly impacted bone chips between a cortical layer and a metal implant have a much lower wash-out rate than a porous block placed into a well bleeding spongiostic area.

The present disclosure shows that the negative feedback from the accumulation of the drug in a small volume just marginally affects the release kinetics so the spatial effect probably plays a limited role in this question. However, it should be noted that our experiment was performed in a laboratory setting and release kinetics with bodily fluids in the presence of metabolizing cells and bacteria are probably different. Therefore, due to the uncertainties inherent in this field of application it is best to load bone grafts with only a low amount of antibiotics to prevent overdosing. The person skilled in the art will be able to use his expertise to determine if higher amounts are tolerable or even necessary.

As a comparison, we estimated the total daily doses potentially released from bone grafts with selected combinations used in the present study (FIG. 4). We applied the femoral head graft as a more or less standard 'dose' of bone grafting material frequently applied in orthopedics. These estimations are based on data gained in vitro, so these can only be considered as rough estimates. The calculations show that the implantation of one femoral head coated with either antibiotics can release a significant percentage of the daily iv dose during the first day but the dose goes below 10% in the long term. Therefore, in case large antibiotic bone grafts are implanted it is recommended to set the systemic antibiotic dosing based on close monitoring of serum levels for a few days after surgery. The 10 mg/ml starting concentration of antibiotic, which was applied in the present study, and is also relevant according to the literature of local antibiotic drug release products regarding both amoxicillin (Xu et al. J Control Release, 2008. 127(2): p. 146-53) and vancomycin (Lepretre et al Biomaterials, 2009. 30(30): p. 6086-93) so these calculations have some relevance towards other antibiotic bone substitutes as well.

Human cancellous bone allografts were chosen as the basic implant for its known endogenous consistence and structure, bone is also biocompatible, porous, osteoconductive, biodegradable. Although grafting materials, which are suitable cannot be limited to bone, porous biocompatible grafting materials include tricalcium phosphate, calcium sulfate, hydroxyapatite, ceramics and mixtures of these materials, mainly all forms of grafting materials that are intended for implant and surgical use.

The size of the grafts may be approximately 0.02 $cm^3$ to 100 $cm^3$.

The person skilled in the art will be readily able to adapt different cancellous matrix materials to practice the present invention.

As biologically active materials, which enhance cell migration and growth we used human derived growth factors (proteins). These mixtures mainly consisting of proteins were derived from human blood with various separation techniques. According to Stacie G. Boswell et al. (Arthroscopy. 2012 March; 28(3):429-39) growth factor peptides include PDGF, TGF-/315 vascular endothelial growth factor, basic fibroblast growth factor (bFGF), and epidermal growth factor.

Exemplary biologically active ingredients may further include other materials to enhance cell adhesion and growth, such as albumin, platelet rich plasma (PRP), platelet pure plasma (PPP) and platelet rich fibrin (PRF). The complex blood separation products may contain cell growth and/or cell migration enhancing agents. The person skilled in the art will be able to select a blood separation product that fits the tissue growth requirements the best.

The biologically active ingredients that decrease bacteria growth were selected from various antibiotics that are already used in the pharmaceutical practice. The antibiotics used in the present invention include three types of antibiotics, the group of beta-lactams, fluorokinolons and glycopeptides. These antibiotics were found to be the most effective in local antibiotic treatment. The person skilled in the art will be able to select the appropriate antibiotics based on the state of the art and his general knowledge. The examples of the present application provide suitable guidance on the simple optimization experiments to be carried out.

In a preferred embodiment, antibacterial agents that can be employed according to the present invention are gentamicin, ciprofloxacin, vancomycin, amoxicillin. The antibiotic coating can be prepared by using solvent evaporation or freeze drying. A preferred process for the coating is the method according to the present invention described below.

The concentration of the antibiotics to be used may be in the range from 0.1 mg/ml to 100 mg/ml. The exact concentration depends on several factors which the person skilled in the art will be able to determine and optimize if necessary. In particular, the bioavailability of the antibiotic used will depend on different factors, such as the chemical nature of the molecule, its interaction with the polymer matrix. Some of these characteristics may be modulated by using derivatized polymer matrix or by encapsulating the antibiotic.

The controlled release of the active component(s) was achieved using biologically available, biocompatible materials. The used materials were the derivatives of chitosan, pectin and alginic acid. Polycaprolactone is used as a well known reference biodegradable polymer that is already used in scaffolds. The expression "controlled release coating" can both be used for film coating or microsphere encapsulation. All these substances are commercially available and from natural sources. Pectin is a commercially available, natural thickening agent polysaccharide. Unfortunately pectin dissolves rapidly in water, so alone it cannot be used as a successful controlled release coating. Sodium alginate (Na-Alg) is the sodium salt of alginic acid that can be extracted from brown algae. Na-Alg is used in the food and pharmaceutical industry. Sodium alginate dissolves in water but with the usage of $Ca^{2+}$ containing solution, water insoluble calcium alginate (Ca-Alg) gel can be formed.

The Controlled release coating may consist of chitosan, alginic acid, pectin or a mixture of at least two of these materials. The coating may be prepared by any known process. In preferred embodiments, the coating is produced by using a film casting method, or with microencapsulation. An especially preferred method of coating is the method according to the present invention, as described below and in the examples section.

When using certain types of active agents (such as drugs that are acids or acidic salts) the release of the agent may be comparable or even faster when we used chitosan than in the absence of a polymer coating. This can be explained with the solubility of chitosan. This polymer is only soluble in acidic media and thus the use of chitosan as a delivery vehicle for sustained release is not suitable for these kinds of agents. The person skilled in the art will be able to determine, based on the physico-chemical properties of the active agent, the type of polymer coating to be used.

Most of the time alginate is used in loaded beads (Ueng et al. J Orthop Res. 2004; 22:592-599) or microspheres (Joshi et al. Acta Biomater. 2011; 7:3955-3963) or composites (Balaure et al. Int J Pharm. 2013; 441:555-561) in the prior art. The invention is based on the discovery that water soluble Na-alginate is suitable to form an approximately even film coating on the surface of such a porous structure as a bone. Surprisingly this coating can be converted to the water insoluble Ca-Alg in-situ on the structure of the applied tissue substitute material and this way it is possible to construct a layer by layer film coating. Using this method we were able to achieve long-term release successfully when we produced an insoluble Ca-alginate film coating. Due to production process and the uneven bone structure the thickness of the alginate film was probably not always uniform on the surface of the bone. This may or may not be a problem for any given medical application, however it is within the qualifications of the ordinary person skilled in the art to carry out the necessary optimization tasks in this context.

As it is apparent from the experimental results, in addition to the polymer, the identity of the active agent plays significant role in the controlled release. Rather, the interaction between the physic-chemical properties of the polymer and the active agents will determine the retention rate of the polymer matrix with respect to the active agent. In this context, although the coatings used did little difference for amoxicillin, both ciprofloxacin and vancomycin proved to be suitable for sustained release bone graft formulations in our experiments. The person skilled in the art will be able to find out the appropriate conditions to achieve the desired level of sustained release. However, the drug delivery period of at least 28 days shown herein should be enough for the long-term antibacterial effect required for the eradication of implant-related infections. According to our measurements, the MIC value of vancomycin was 0.2 µg/ml for *Enterococcus faecalis* (data not shown), which was 28 times below the measured vancomycin concentration on the 50th day, indicating that this dose is probably enough for keeping the graft free of bacteria and may even penetrate the surrounding tissues for a therapeutic effect.

The novelty of the present invention lies at least in part in the formulation (the discovery of constructing a layer by layer water insoluble film from a water soluble film) and the used ratios of the components. In particular, according to our findings, the novelty is also in the alginate pectin ratio, the optimal Na-Alg is between 70-90% and the pectin is between 10-30%. With the fine adjustment of the ratios, the antibiotic liberation can be adjusted from a couple of days to weeks. The graft according to the present invention generated according to a specific process.

The sequence of generating the coatings is a stepwise procedure.

The first step is preparing a homogenous antibiotic coating with freeze drying solvent evaporation or vacuum evaporation, or any other suitable method known in the art. In this step the antibiotic can be an aqueous solution, organic solution, or suspension. Any other additive, such as biologically active factors, may also be included at this step. The biologically active additives may be combined in this step, and/or different additives may be used in different steps, such as the later described second or third steps. The person skilled in the art will be readily able to determine the use and order of biologically active additives.

In the following step a water-soluble film coating (FC) is prepared that is either sprayed or casted on the surface of the bone that was coated with antibiotic in the prior step. This FC includes the biocompatible polymer material. The materials may be chitosan, pectin, or alginic acid, or derivatives thereof, or mixtures of at least two of the polymers in a predetermined ratio.

In a preferred embodiment, the FC contains a mixture of pectin and Na-Alg. In a particularly preferred embodiment, the specified ratio of pectin and Na-Alg is within the range of 70 to 90% for Na-Alg and within the range of 10 to 30% for pectin. The person skilled in the art will be readily able to fine tune the exact ratios to allow for the controlled release of the antibiotic used in the first step.

After the bone is coated with the FC, the FC needs to be dried to finish the second step. Drying can be accomplished by placing the samples in a drying chamber or exsiccator, it is also a possibility to use moderate heating and vacuum to increase the water content evaporation.

The last step of the procedure is converting the water soluble Na-Alg part of the FC into water insoluble Ca-Alg with the usage of a Ca ion containing solution, which is sprayed onto the dry FC coating. The concentration of the Ca solution can be varied, generally is within the range of 1 to 20%.

This partially water insoluble FC coating also needs to be dried. The drying conditions may be the same or different from the ones used at the end of the second step. As a result of this drying step, the final partially water insoluble FC on the antibiotic bone is prepared.

To summarize the process, the three steps of the preparation includes several key novel features, such as the polymer-ratio of the FC and the way the conversion of water soluble FC into water insoluble FC is achieved in situ.

There are several types of bone disease that can be treated by antibiotic bone substitutes. The three main categories are:

1, Prevention of bone infection. e.g. Surgery, contaminated wounds, open fractures, implantation of any foreign material, presence of any foreign material, filling the cavity of bone cysts, treatment of aseptic non-union.

2, Prevention of re-infection. e.g. Revision surgery after septic complications, reconstructive surgery after traumatic or other bone loss, treatment of posttratumatic or post-septic non-union.

3, Treatment of bone infection. e.g. Acute or chronic osteomyelitis, ostitis, septic non-union, septic implants or prosthetic devices or any other foreign material, including projectiles, etc.

Such bacterial infections may be caused by e.g. *Staphylococcus epidermidis, Staphylococcus aureus, Enterococcus* infections and *Streptococcus*. These type of infections can be prevented and/or treated by using at least one biologically active substance that decreases bacterial growth, such as any standard antibiotics or a mixture thereof.

The treatment method by using the bone substitute material according to the invention primarily involves providing a tissue graft to the patient. An exemplary procedure is as follows: The patient's injury site (e.g. jaw bone) should be prepared routinely as per surgery. The appropriate length of the grafting material should be estimated before surgery and produced according to the needs. The grafting material shall be fixed to the bone stumps by e.g. bicortical screws. The surgical site needs to be secured and closed, the grafting material will release the biologically active component over the needed time period (e.g. days or weeks).

The present invention is further illustrated by the experimental examples described below; however, the scope of the invention will by no means be limited to the specific embodiments described in the examples.

Materials and Methods

Antibiotic Solution

All chemicals were purchased from Sigma except from vancomycin, which was purchased from Hangzhou API-Chem Technology Co., Ltd., China. The bone blocks were a generous gifts from the West-Hungarian Regional Tissue Bank Freeze-dried femoral head blocks were cut to 0.05±0.01 g cube-shaped pieces.

The antibiotic containing solution was prepared by adding one or more antibacterial agent(s) (e.g. amoxicillin, ciprofloxacin, etc.) to an aqueous solution. The aqueous solution may also contain a suspension that is the growth factor enriched phase of a blood product. The antibacterial agent content is typically between 0.1 mg/ml to 100 mg/ml, we used 10 mg/ml concentration. We can use the mixture when a homogenous solution or suspension is formed this can be achieved with using a magnetic or overhead stirrer. We can also use this technique when the applied antibiotic is lipophilic, but in this case we need to use organic solvents.

Microspheres

The antibiotic content may also be present in the form of microspheres. These microspheres are water insoluble spheres with encapsulated antibiotic content. The production of these spheres is based on converting water soluble alginate solution, which contains antibiotic, into water insoluble alginate solution. This can be done by spraying Na-Alg into a Ca ion containing solution, and so the water insoluble spheres are formed. The spheres can be filtered off, dried and used later as antibiotic bone coating. The spheres may also be formed from chitosan, or any biocompatible polymer that is suitable for the purpose.

Chitosan Based Short-Term Release Coating

Chitosan-based preparations were prepared by using 1 ml aqueous 2% chitosan solution to dissolve the antibiotic. The bone samples were placed in this solution and incubated at room temperature for 24 hours and frozen and lyophilized afterwards in a similar manner as the saturated preparations.

Alginate Based Short-Term Release Coating

Figure 1:
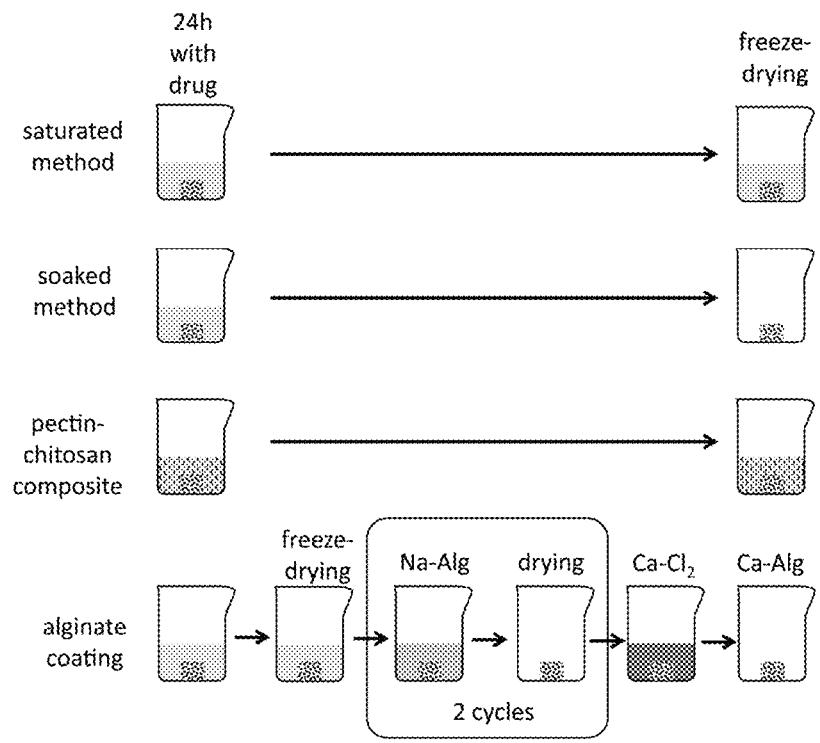
FIG. 1. Coating methods. As a first step, bone allografts were incubated in an antibiotic solution for 24 hours. Subsequently, the soaked graft was removed from the solution and freezed at −80° C. followed by lyophilization for 24 hours using a Labconco Freezone 2.5' freeze-dryer (soaked preparation). In order to maximize the drug content of the graft an alternative approach was also performed when the grafts were frozen while still submerged in the antibiotic solution and the whole system was freeze-dried (saturated preparation). The Na-Alg film was prepared by adding Na-Alg solution on the antibiotic coated freeze-dried bone. Then the graft was dried in an oven. The process was repeated with the dried coated graft turned upside down, thus the double layer Na-Alg film was formed. Sodium alginate was then converted into calcium alginate by Ca ion containing aqueous solution.

Alginate-based preparations should be created in another way since this polymer has a basic pH and antibiotics precipitate in it. First, the bone grafts were coated by the saturated freeze-dried method as described above then a film coating of alginate was created on top of the antibiotic layer. The Na-Alg film was prepared by adding 1 ml 4% Na-Alg solution on the antibiotic coated freeze-dried bone. Then the graft was dried in an oven at 40° C. for 4 hours on teflon plates. The process was repeated with the dried coated graft turned upside down, thus the double layer Na-Alg film was formed. Sodium alginate was then converted into calcium alginate by CaCl2. The Na-alginate coated bone grafts were placed in the 10% CaCl2 solution for exactly 60 seconds then washed with distilled water and dried in an oven at 40° C. The methods for preparing the coatings are presented in FIG. 1.

Antibiotic Release Measurements

The chosen antibiotics (amoxicillin, ciprofloxacin and vancomycin) have characteristic absorbances in the UV range in aqueous solutions, allowing the use of UV spectroscopy to assess the concentrations with a spectrophotometer. The absorbance-concentration diagrams were plotted using all antibiotics and the linear phase of this diagram was used to calculate the concentration from the absorbances according to the Lambert-Beer law (Table 2).

TABLE 2

UV measurement characteristics of the investigated antibiotics

| | Characteristic absorbance (nm) | Linear absorbance-concentration interval |
|---|---|---|
| Amoxicillin | 229 | 0.22-3.7 |
| Ciprofloxacin | 275 | 0.085-2.29 |
| Vancomycin | 280 | 0.06-2.00 |

Measurements of release kinetics were performed by incubating each sample separately in 2 ml of water in a 24 well plate at room temperature. Concentration measurements were performed at regular intervals by removing the supernatant for spectroscopy and replenishing with fresh solvent. The frequency of solution changes and the length of the experiments were determined by preliminary experiments and set in a way that optimal kinetic curves can be constructed from the data. In a separate experiment with Ca-Alg coated amoxicillin grafts, the medium was pipetted back onto the graft after each measurement in order to evaluate the effect of drug accumulation in the medium on the release kinetics. Statistics were carried out using Graph-Pad Prism 5.0 software. All data were expressed as means±SEM (n=3).

Freeze Drying

Freeze drying was applied as a method to prepare antibiotic coating. In this method 1 $cm^3$ or 2 $cm^3$ of aqueous antibiotic solution is incubated with the bone for 10 hours. The mixture was then put in a refrigerator at −80° C. for 4 hours. The frozen samples were freeze dried at −50° C. and 2.1 Pa reduced pressure for 12 hours. After 12 hours of freeze drying, the bone was taken out from the freeze dried matrix, the drug formed a dense coating all over the surface of the bone.

Film Casting

The antibiotic coating was further modified with a controlled release film. This was achieved by adding 1 ml of the film coating material on the bone, which was placed in a teflon plate. The plate was put in an oven with the temperature set to 40° C. After 4 hours of drying, the plate was taken out, and the excess film coating was cut off the bone. The procedure with the bone after turning it upside down was repeated again. After drying it and cutting the excess film off again, the film and antibiotic coated bone was soaked in 10% $Ca^{2+}$ containing solution for 60 seconds. The calcium ions convert the water soluble Na-Alg to water insoluble Ca-Alg, and so a controlled release coating can be formed. If we used more than one component to produce the film (composite film) the ratio of the materials can also change the rate of antibiotic release (e.g. 40% Na-Alg and 60% pectin). The modification with calcium only affects the alginate part, so the reduced amount of alginate enhances the release of the used antibiotic.

Example 1: Short Term Antibiotic Release

The drugs were highly soluble in water and were suitable to be stored at room temperature without any decomposition thus all the drugs were successfully applied on the surface of the bone. The original concentration of the antibiotic solutions used for incubating the bone grafts correlated with the amount of antibiotics on the bone surface estimated by the released total amount of drugs. 10 mg/ml starting solution was used in the experiment.

Figure 2:
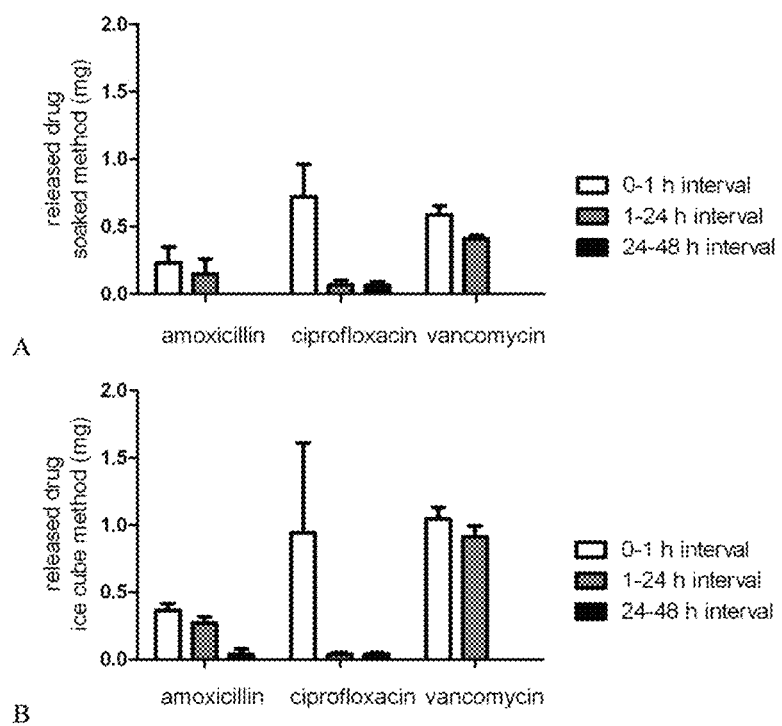
FIG. 2 shows the short-term release of the antibiotics over a 48 hour period. prepared by the soaked or the saturated method.

Simple freeze-drying of antibiotics on the surface of bone grafts did not result in a sustained release of the compounds. Although minor differences were observed among the three antibiotics, each one is completely released within 48 hours (FIG. 2). Maximizing the antibiotic loading on the grafts by freezing them in the solution (saturated method) before lyophilization did not improve the release kinetics only the overall amount of antibiotics on the graft (FIG. 2B). Using a chitosan additive with the antibiotics did not significantly prolong the release of the drugs from the surface.

Example 2: Long Term Antibiotic Release

Figure 3:
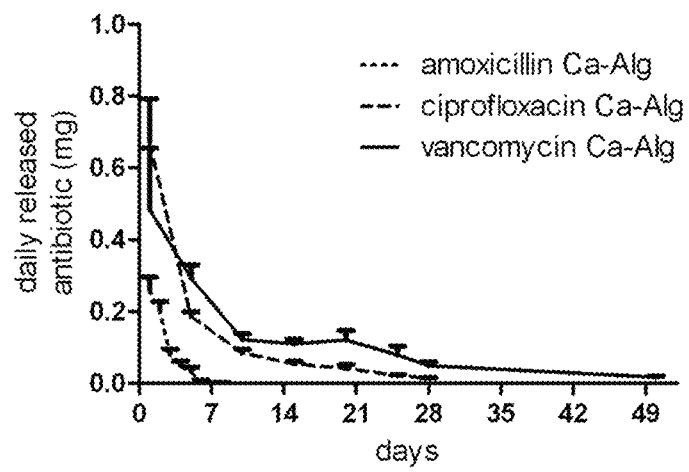
FIG. 3 Release profile of amoxicillin, ciprofloxacin or vancomycin with sustained release Ca-Alg film coating (n=3). Although the coating method was the same in each case, the effective release term is different among the three drugs with amoxicillin lasting up to 8 days, ciprofloxacin up to 28 days while vancomycin reaches 50 days.
Figure 4:
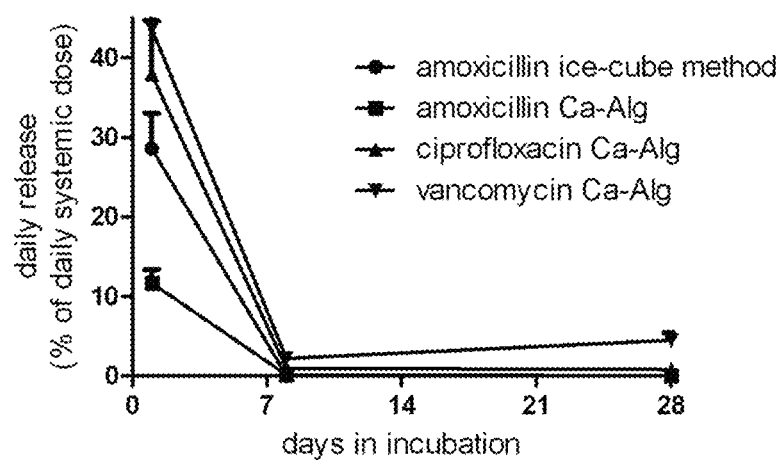
FIG. 4. Calculated daily release of antibiotics from one implanted femoral head graft. Values are expressed as percentages of the daily recommended iv dose (amoxicillin 2000 mg/day, ciprofloxacin 1600 mg/day, vancomycin 1000 mg/day). Please note that values are calculated from in vitro data, not actual in vivo implantations, which may vary significantly due to the type of grafting and the individual difference among patients. Nonetheless, the data indicate that the antibiotics implanted with the bone grafts may significantly increase the daily systemic dose only for the first day. Therefore, in case of large volumes of antibiotic bone grafts are implanted the systemic dosing must be carefully monitored during the first few postop days.

Using a Ca-Alg film layer it was possible to reach a long-term sustained-release antibiotic coating. Interestingly, the type of antibiotic significantly affected the rate of drug release from the same type of coating. Amoxicillin was completely released within 8 days, ciprofloxacin within 28 days, while vancomycin was the longest with 50 days (FIG. 3). The amount of active ingredient released on the first day was approximately the same as the amount from the antibiotic bones, which did not contain Ca-alginate (FIG. 2). The total quantity of dissolved antibiotics over the 8, 28, or 50 or day period depending on the respective antibiotic was approximately the same than those without alginate coating, indicating that the amount of total antibiotic content did not increase only the release rate has changed (FIG. 3).

To summarize the long-term release experiment, altogether 0.64±0.07 mg amoxicillin was eluted from the surface of 50 mg bone allograft, with complete dissolution in 8 days. In case of ciprofloxacin, 1.08±0.11 mg was the total eluted amount within 28 days. Vancomycin had the longest elution time for over 50 days during which 1.66±0.31 mg antibiotic was released altogether.

Example 3

50 mg bone chips were freeze dried in an aqueous solution that contained 10 mg/ml of vancomycin. One milliliter of 4% Na-alginate (Na-Alg) was added to the freeze dried bone in a teflon plate and the water content was allowed to evaporate in an oven at 40° C. The coating with Na-Alg was repeated once again. After the coating dried we soaked the coated bone in 10% $CaCl_2$ solution for 60 seconds, to form water insoluble Ca-alginate (Ca-Alg) and the bones were dried again. Finally the dried Ca-Alg coated bone was irradiated with UV light to be sterile.

Example 4

100 mg bone was freeze dried in 10 mg/ml vancomycin solution. 1 ml 4% Na-Alg added dropwise to the bone and dried in an oven at 40° C. to form a composite film. The film coated bone was covered again with the composite film and the excess film residues were cut off. After drying, the coated bone was soaked in 10% calcium ion containing solution Example 5

50 mg bone was freeze dried in 10 mg/ml ciprofloxacin solution. 4 ml 4% Na-Alg was mixed together with 1 ml 4% pectin to form a composite viscous solution. This viscous solution was added dropwise to the bone and dried in an oven at 40° C. to form a composite film. The film coated bone was covered again with the composite film and the excess film residues were cut off. After drying, the coated bone was soaked in 10% calcium ion containing solution. This method enables to change the release mechanism.

Example 6

50 mg bone was freeze dried in 50 mg/ml amoxicillin solution. 2 ml 4% Na-Alg was mixed together with 2 ml 4% pectin to form a composite viscous solution. This viscous solution was added dropwise to the bone and dried in an oven at 40° C. to form a composite film. The film coated bone was covered again with the composite film and the excess film residues were cut off. After drying, the coated bone was soaked in 10% calcium ion containing solution. This method enables to change the release mechanism and reduce the drug release time.

Example 7

1 ml aqueous 2% chitosan solution was used dissolve 10 mg gentamicin. The 50 mg bone sample was placed in this solution and incubated at room temperature for 24 hours. After the incubation the solution that contained the bone sample (saturated method) was frozen and lyophilized afterwards. After freeze drying the bone was taken out from the well together with the chitosan-antibiotic mixture that was in part attached to the surface of the bone. Thus a short-term drug release coating was prepared.

Example 8: Pectin-Alginate Two Component Film 0.8 ml 4% Na-Alg and 0.2 ml pectin was mixed together until a homogenous gel was formed. The mixture was poured onto the surface of a previously prepared freeze dried chitosan matrix and dried in an oven at 40° C. to form a composite film. The film was soaked in 5% calcium ion containing solution for 2 minutes and dried again afterwards. Thus a 2 component partly water insoluble film was produced.

Example 9: Pectin-Alginate Two Component Microsphere 0.9 ml 4% Na-Alg and 0.1 ml pectin with 50 mg vancomycin was mixed together until a homogenous gel/suspension was formed. The mixture was poured into a syringe. The content of the syringe was added at a constant dropwise rate into a 15% calcium ion containing solution for 30 seconds and filtered off immediately and dried afterwards in an oven at 40° C. Thus a 2 component partly water insoluble microsphere was produced.

The invention claimed is:
1. A tissue substitute material for implantation, comprising (a) a substrate to be implanted covered with (b) a controlled release coating containing (c) at least one biologically active substance that decreases bacterial growth,
wherein the (b) controlled release coating is a bioavailable, biocompatible polymer material comprising alginate and pectin;
wherein the (c) at least one biologically active substance that decreases bacterial growth is selected from the group consisting of antibiotics and a mixture thereof, and
wherein at least one water soluble part of the polymer material has been selectively converted into water insoluble form.

2. The tissue substitute material according to claim 1, wherein the polymer material contains water insoluble Ca-alginate.

3. The tissue substitute material according to claim 2, wherein the substrate is bone allograft.

4. The tissue substitute material for implantation according to claim 1, which is a bone substitute material for implantation, wherein the substrate is bone allograft, and
wherein the (b) controlled release coating is a bioavailable, biocompatible polymer material consisting of alginic acid and pectin.

5. The tissue substitute material according to claim 1, wherein the substrate is a known tissue substitute selected from the group consisting of implants made from metal, plastic, and standalone polymer material suitable for the preparation of the coating.

6. The tissue substitute material according to claim 1, wherein the (b) controlled release coating is alginic acid pectin copolymer.

7. The tissue substitute material according claim 1, wherein the (b) controlled release coating essentially consists of alginic acid within the range of 70 to 90% and pectin within the range of 10 to 30%.

8. The tissue substitute material according to claim 1, wherein the (c) at least one biologically active substance that decreases bacterial growth is selected from the group consisting of gentamicin, ciprofloxacin, vancomycin, amoxicillin.

9. The tissue substitute material according to claim 1, further comprising other biologically active ingredients to enhance cell migration, adhesion and growth.

10. The tissue substitute material according to claim 1, wherein the biologically active ingredient to enhance cell migration, adhesion and growth is selected from the group consisting of growth factors including PDGF, TGF-/315 vascular endothelial growth factor, basic fibroblast growth factor (bFGF), and epidermal growth factor; albumin, platelet rich plasma (PRP), platelet pure plasma (PPP) and platelet rich fibrin (PRF) and blood separation products that contain cell growth and/or cell migration enhancing agents.

11. A method for preparing a tissue substitute material for implantation according to claim 1, comprising
(a) preparing a homogenous coating on a substrate to be implanted from at least one biologically active substance that decreases bacterial growth selected from the group consisting of antibiotics and a mixture thereof;
(b) preparing a film coating from the water-soluble monomers of a biocompatible polymer material of alginic acid in combination with pectin;
(c) drying the water-soluble film coating;
(d) converting the water soluble film coating into water insoluble film coating;
(e) drying the water-insoluble film coating.

12. The method according to claim 11, wherein the tissue is a tissue from the musculoskeletal system.

13. The method according to claim 12, wherein the substrate is bone allograft.

14. The method according to claim 11, wherein the substrate is alginate beads.

15. The method according to claim 11, wherein the antibiotic coating is prepared in step (a) by freeze drying, solvent evaporation or vacuum evaporation.

16. The method according to claim 11, wherein the film coating is prepared in step (a) spraying or casting.

17. The method according to claim 11, wherein the drying in step (c) and/or (e) is accomplished in a drying chamber or exsiccator, or by using moderate heating and vacuum.

18. The method according to claim 11, wherein the biocompatible polymer material selected is alginic acid pectin copolymer, wherein the alginic acid within the range of 70 to 90% and pectin within the range of 10 to 30%, and wherein in step (d), the conversion of the soluble film coating into water insoluble film coating is accomplished by using a $Ca^{2+}$ ion containing solution.

19. The method according to claim 11, further comprising the inclusion of other biologically active ingredients to enhance cell migration, adhesion and growth into the biocompatible polymer coating material, selected from the group consisting of growth factors including PDGF, TGF-/315 vascular endothelial growth factor, basic fibroblast growth factor (bFGF), and epidermal growth factor; albumin, platelet rich plasma (PRP), platelet pure plasma (PPP) and platelet rich fibrin (PRF) and other blood separation products that contain cell growth and/or cell migration enhancing agents.

20. A method for treating or inhibiting bone infection, said method comprising implanting the tissue substitute material of claim 1 in the form of a graft in a patient in need thereof.

* * * * *